(12) United States Patent
Joshi et al.

(10) Patent No.: US 6,957,779 B2
(45) Date of Patent: Oct. 25, 2005

(54) FOLDABLE, REFILLABLE, SUSTAINED-RELEASE FLUID DELIVERY SYSTEM

(75) Inventors: Ashok V. Joshi, Salt Lake City, UT (US); Truman Wold, Salt Lake City, UT (US); John J. McEvoy, Salt Lake City, UT (US)

(73) Assignee: Microlin, L.C., Salt Lake City, UT (US)

( * ) Notice: Subject to any disclaimer, the term of this patent is extended or adjusted under 35 U.S.C. 154(b) by 158 days.

(21) Appl. No.: 10/300,729

(22) Filed: Nov. 20, 2002

(65) Prior Publication Data

US 2003/0132305 A1 Jul. 17, 2003

Related U.S. Application Data

(63) Continuation-in-part of application No. 09/989,552, filed on Nov. 20, 2001, now abandoned, and a continuation-in-part of application No. 09/989,616, filed on Nov. 20, 2001, now abandoned.

(51) Int. Cl.[7] .............................. A24F 25/00; A61L 9/04
(52) U.S. Cl. .............................. 239/43; 239/37; 239/44; 239/57
(58) Field of Search ............................ 239/43, 37, 44, 239/57, 40–42, 136, 309, 302; 222/83, 181.2, 181.3

(56) References Cited

U.S. PATENT DOCUMENTS

| | | | | |
|---|---|---|---|---|
| 696,512 A | * | 4/1902 | Strauss .................... 239/56 |
| 959,111 A | | 5/1910 | Buckland ................ 239/42 |
| 1,661,547 A | * | 3/1928 | Reefer .................... 239/42 |
| 4,339,079 A | | 7/1982 | Sato et al. ................. 239/43 |
| 4,526,320 A | * | 7/1985 | von Philipp et al. ......... 239/43 |
| 4,537,351 A | * | 8/1985 | Wilson ..................... 239/43 |
| 4,840,773 A | * | 6/1989 | Wade ..................... 422/124 |
| 4,917,301 A | * | 4/1990 | Munteanu ................ 239/43 |
| 4,995,555 A | * | 2/1991 | Woodruff ................. 239/43 |
| 5,000,383 A | * | 3/1991 | van der Heijden ......... 239/47 |
| 5,810,253 A | * | 9/1998 | Ohayon .................... 239/43 |
| 5,839,221 A | | 11/1998 | Ron et al. ................. 43/132.1 |
| 5,928,194 A | | 7/1999 | Maget ..................... 604/141 |
| 5,938,640 A | * | 8/1999 | Maget et al. .............. 604/145 |
| 6,109,539 A | | 8/2000 | Joshi et al. ................. 239/43 |
| 6,331,172 B1 | * | 12/2001 | Epstein et al. ............. 604/82 |
| 6,569,387 B1 | | 5/2003 | Furner et al. .............. 422/123 |

* cited by examiner

Primary Examiner—Darren W Gorman
(74) Attorney, Agent, or Firm—Factor & Lake

(57) ABSTRACT

The invention described herein is a framed fluid delivery device that is made up of a fluid-delivery cartridge for the timed-release delivery of a fluid contained therein, and a frame assembly for retaining the fluid delivery cartridge. The frame assembly is made up of a base portion that facilitates the delivery of fluid released from the fluid-delivery cartridge, at least one side panel associated with the base, and that secures the fluid-delivery cartridge within the frame assembly proximate the released fluid delivering means. Additionally, a fluid delivery device is disclosed that includes a fluid-delivery cartridge for the timed-release delivery of a fluid contained therein, the cartridge having a bottom, a top, and sides, and a dispersion pad positioned proximate the bottom of the fluid-delivery cartridge, wherein the dispersion pad at least partially surrounds the sides of the fluid-delivery cartridge.

45 Claims, 7 Drawing Sheets

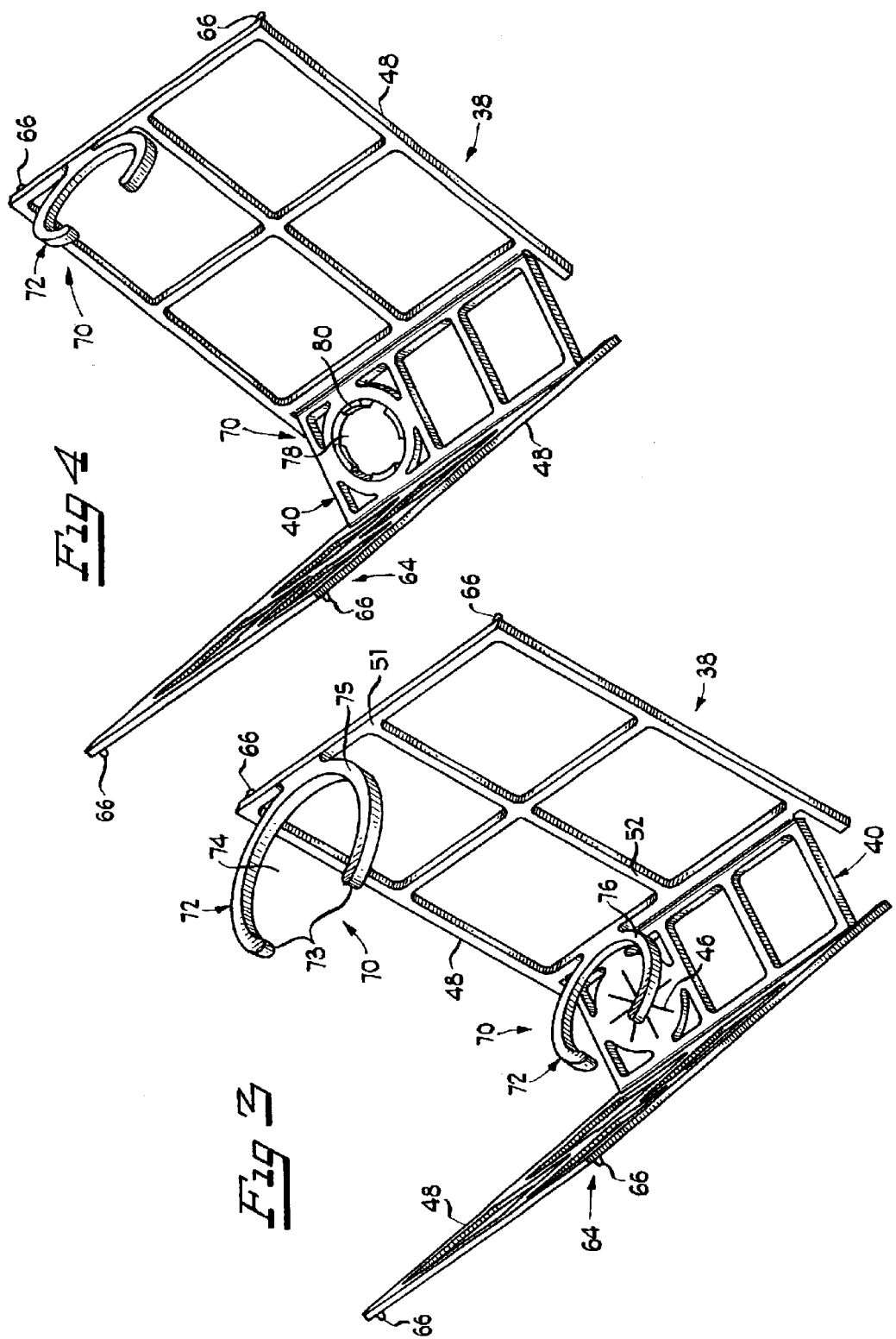

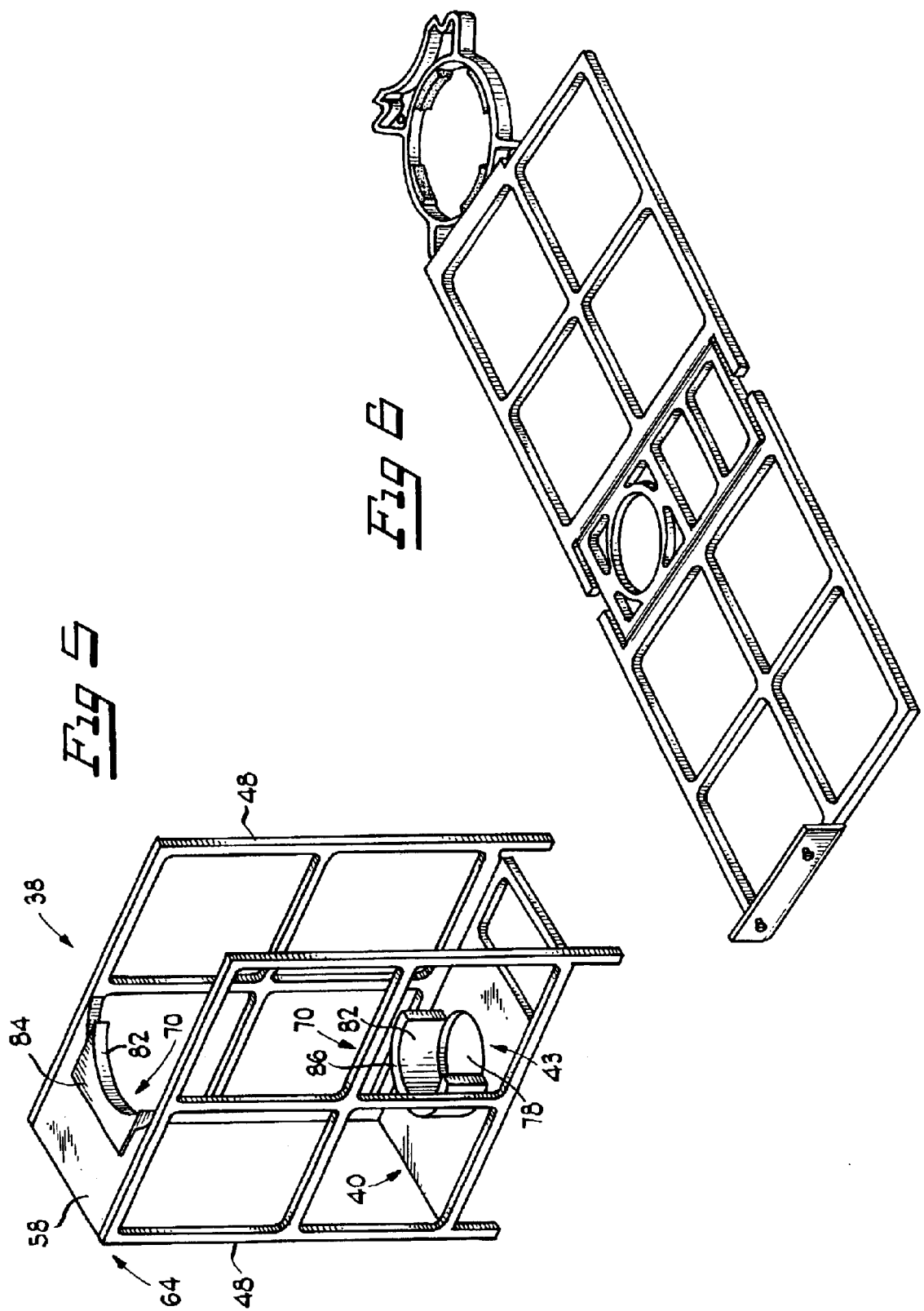

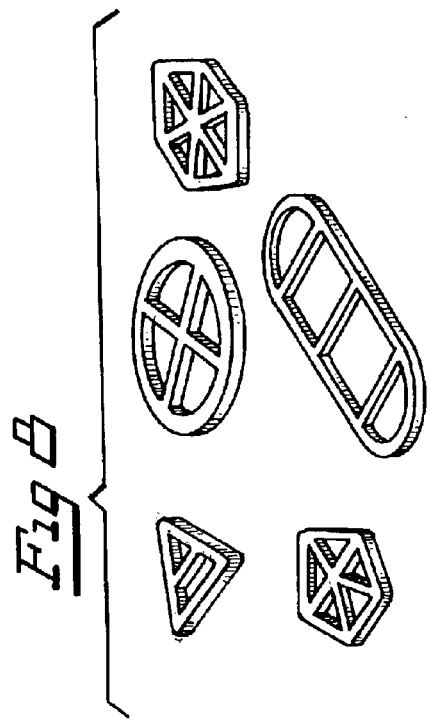
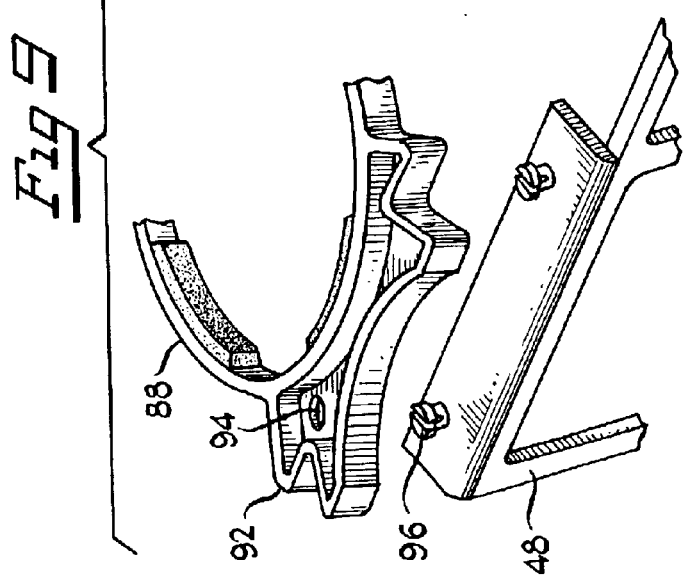
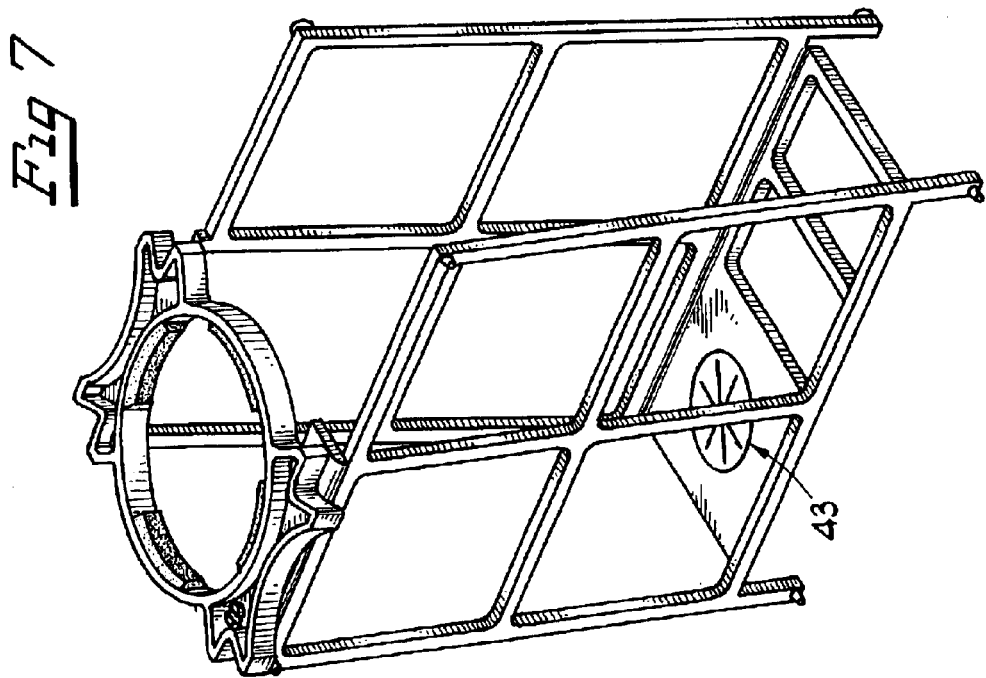

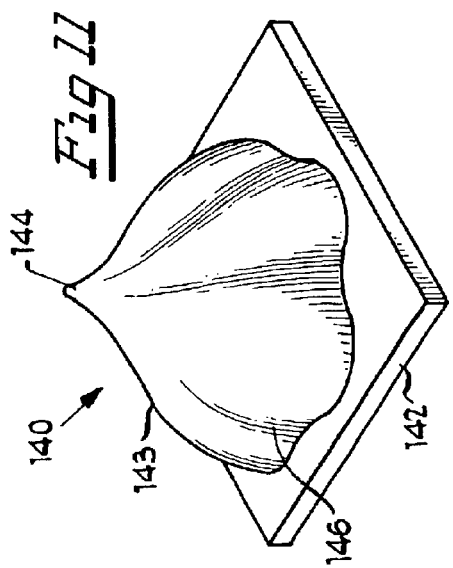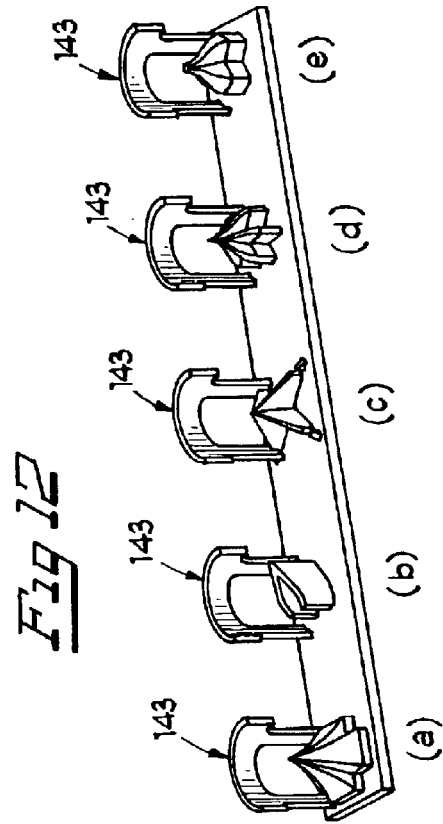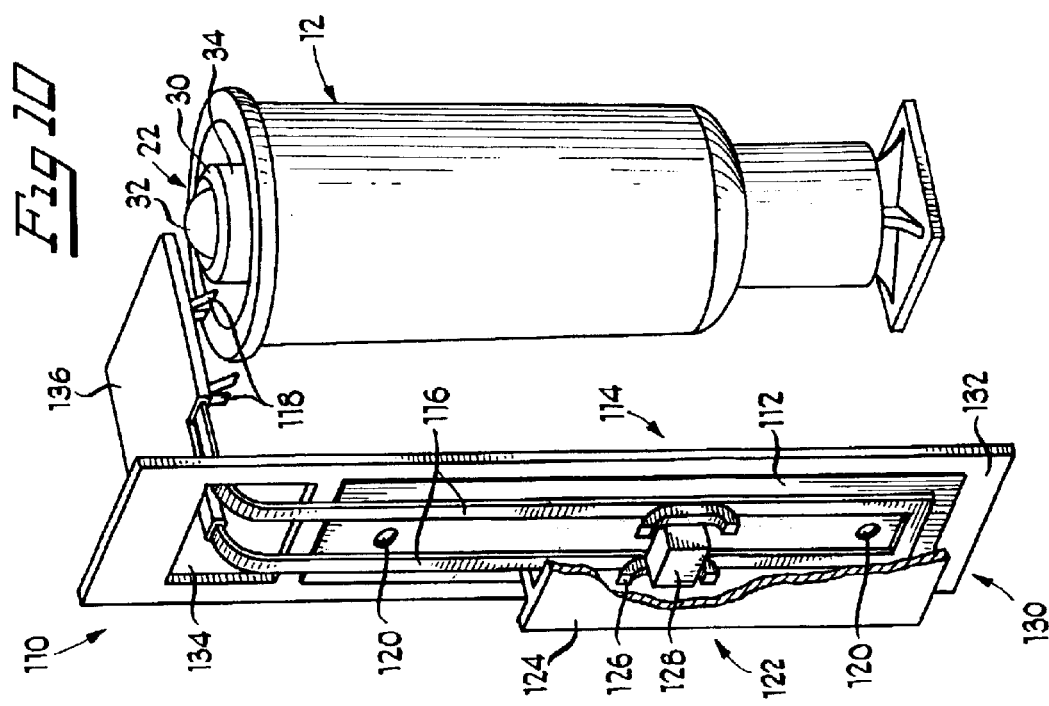

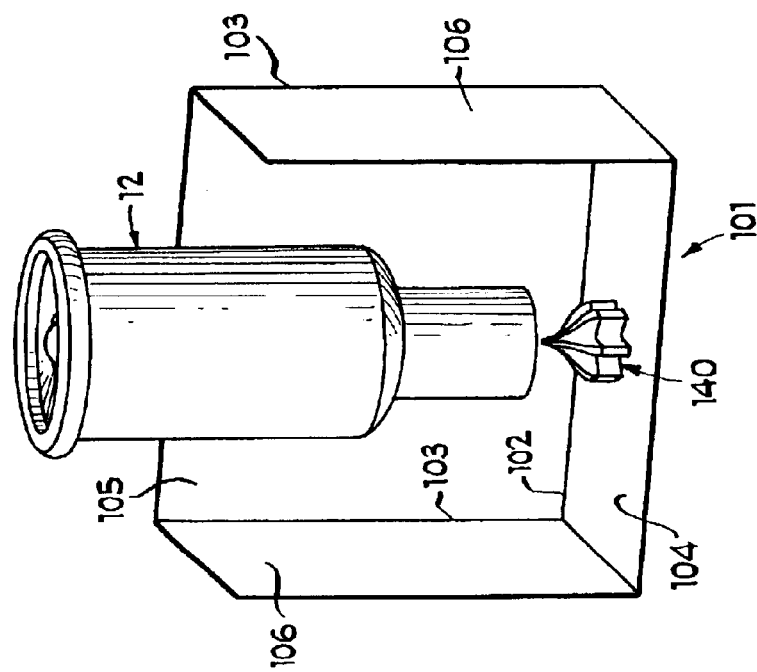
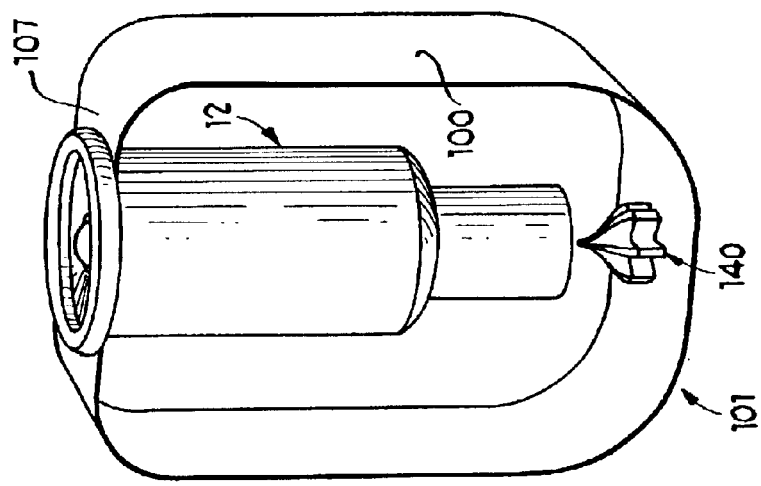
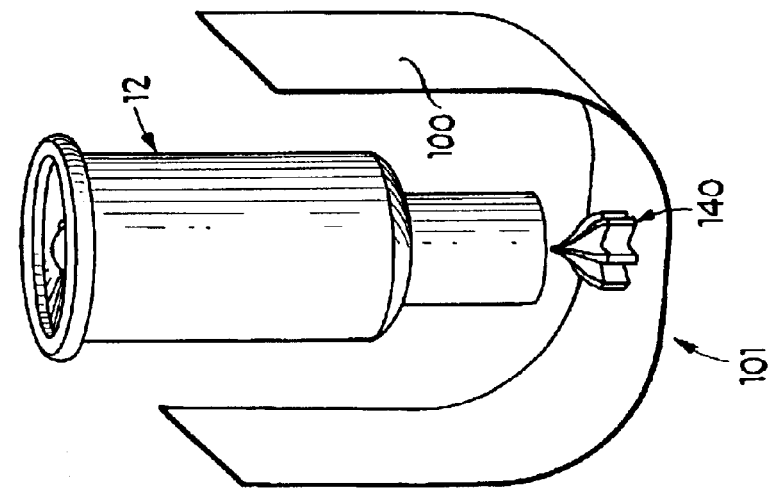

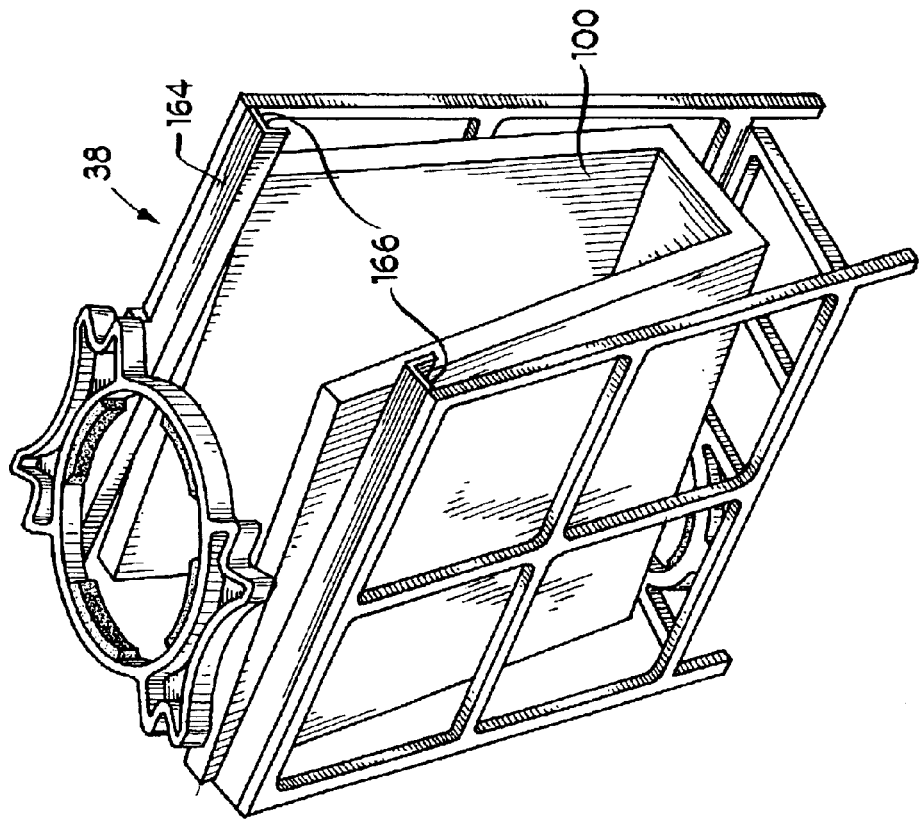
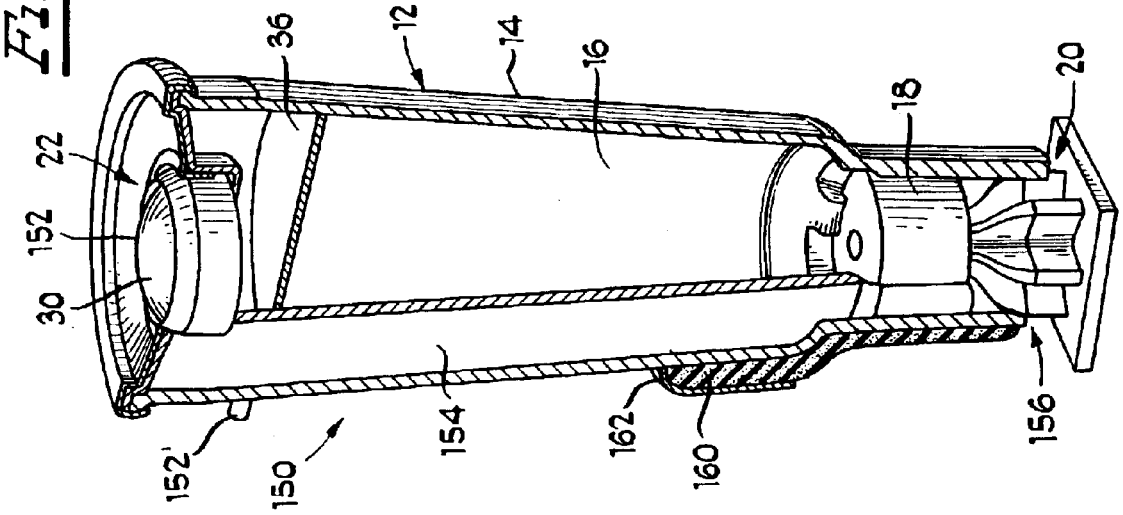

FOLDABLE, REFILLABLE, SUSTAINED-RELEASE FLUID DELIVERY SYSTEM

Continuation-in-part (CIP) of prior application Ser. No. 09/989,616, filed Nov. 20, 2001, now abandoned Ser. No. 09/989,552, filed Nov. 20, 2001, now abandoned.

BACKGROUND OF THE INVENTION

1. Field of the Invention

The present invention relates generally to the delivery of volatile liquids over a period of time to a surrounding area of space, and particularly to structures capable of retaining a fluid delivery device capable of releasing a fluid over time, and facilitating the improved release of volatile liquids therefrom.

2. Background Art

The need for the sustained-release of volatile fluids has been known for some time. In particular, a number of industries have focused on new and innovative ways to provide improved structures for the delivery of known volatile substances. For example, air freshening agents and insecticides have been delivered over a long period of time using devices such as plug-in devices, candles, aerosol sprays and evaporating pools.

One particular structure has been used to deliver these volatile substances successfully. This structure, known as a time-release fluid delivery cartridge, contains a volatile fluid that is delivered from the cartridge onto an eminator pad located directly underneath the cartridge. The eminator pad provides a medium for retaining the fluid after its release from the cartridge. As the fluid is volatile in nature, the more surface area of the fluid contact with air, the more volatilization occurs, and the higher the release of the fluid into the surrounding air.

These known devices, however, have several drawbacks. The cartridges and emanator systems used in these delivery devices lack a secure retention system that would enable these devices to be placed in a variety of housings and to be easily handled during use. Further, as the currently-known devices retain the released liquid solely below the cartridge, a significant degree of improved volatilization is being missed. Finally, the regulation of the operation of the device, both in initiation and in continued operation, has not, as of yet, been addressed to a significant degree.

Therefore, it is an object of this invention to provide a secure retaining means for insertion and retention of fluid delivery cartridges, and for easier user handling of these cartridges.

It is also an object of this invention to provide an improved dispersion system (emanator) for the volatile fluid released from the cartridge.

It is a further object of this invention to provide an apparatus for securing the dispersion system relative to the cartridge.

It is yet a further object of this invention to provide a means for regulating the operation of the cartridge so as to allow the fluid delivery rate to be adjusted during operation.

It is likewise an object of this invention to provide an improved means of releasing fluid from the fluid cartridge so as to maximize both fluid flow and fluid dispersion.

These and other objects will become apparent to one of ordinary skill in the art given the following specification, claims and drawings.

BRIEF DESCRIPTION OF THE DRAWINGS

FIG. 3 comprises a perspective view of an alternative embodiment of the frame assembly;

FIG. 4 comprises a perspective view of yet another alternative embodiment of the frame assembly;

FIG. 5 comprises still another perspective view of another alternative embodiment of the frame assembly;

FIG. 6 comprises a perspective view of the frame assembly in an unfolded position;

FIG. 7 comprises a perspective view of the frame assembly having an alternative embodiment of the delivery facilitating means;

FIG. 8 comprises perspective views of possible base portion shape alternatives;

FIG. 9 comprises a close up perspective view of a connection between a collar and a side panel;

FIG. 10 comprises a perspective view of a fluid delivery system that incorporates a potentiometer;

FIG. 11 comprises a perspective view of a possible embodiment of a piercing member;

FIGS. 12(a)–12(e) comprises perspective views of alternative shapes of the piercing member;

FIG. 13 comprises a perspective view of one embodiment of a dispersion pad with the fluid delivery cartridge;

FIG. 14 comprises a perspective view of another embodiment of a dispersion pad with the fluid delivery cartridge;

FIG. 15 comprises yet another perspective view of a dispersion pad with the fluid delivery cartridge;

FIG. 16 comprises a cut-out view of a fluid delivery cartridge; and

FIG. 17 comprises a perspective view of a frame assembly having a folded and trapped dispersion pad therein.

SUMMARY OF THE INVENTION

Figure 2:
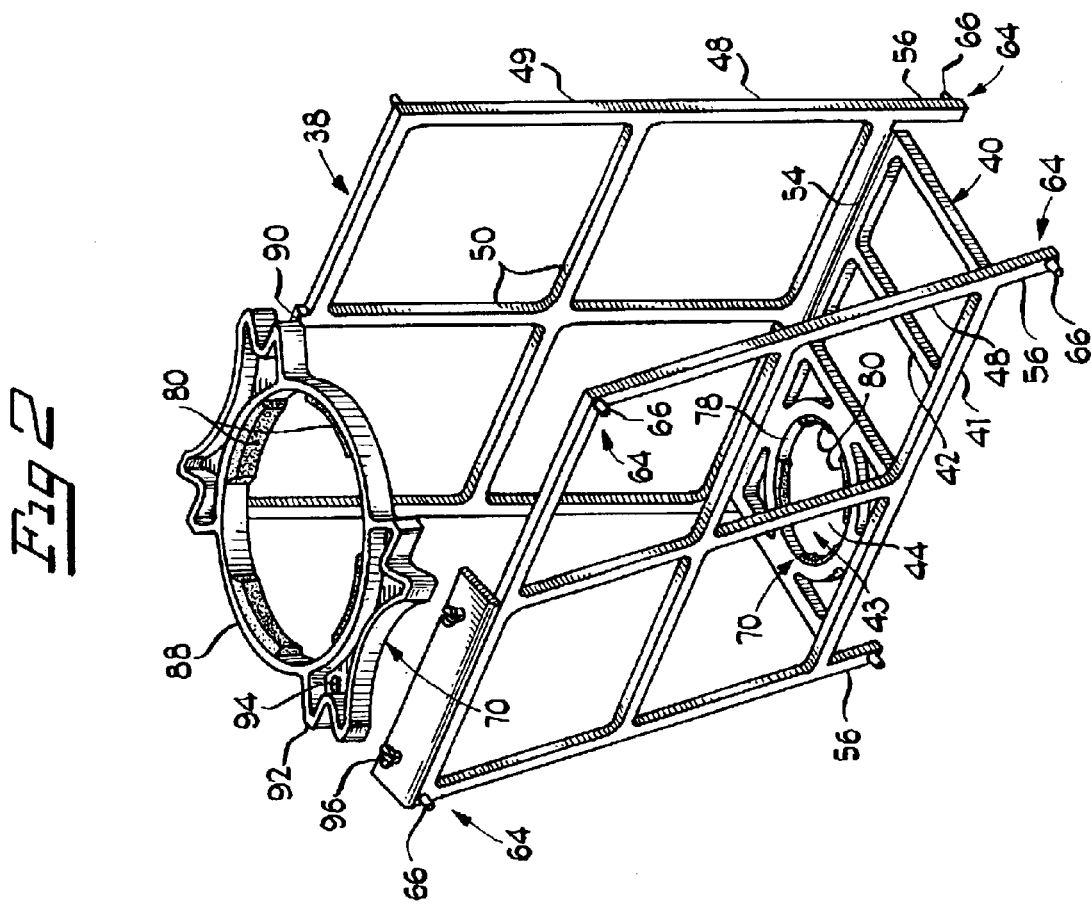
FIG. 2 comprises a perspective view of a frame assembly as described herein.

The present invention is shown and described herein as a framed fluid delivery device that, at a minimum, has a fluid-delivery cartridge for the delivery of a fluid contained therein over a period of time, and a frame assembly for retaining the fluid delivery cartridge, comprising means for securing the fluid-delivery cartridge within the frame assembly. The frame enables the cartridge to be securely retained within the frame assembly for easy handling and storage.

Preferably, the frame assembly consists of a base portion having a means for facilitating the delivery of fluid released from the fluid-delivery cartridge, and at least one side panel, but preferably at least two side panels, associated with the base, wherein the securing means secures the fluid-delivery cartridge proximate the released fluid delivering means. The side panels may also have leg extensions depending therefrom. The side panels may be either hingedly or fixedly associated with the base portion. If the side panels are hingedly attached, they enable the frame assembly to begin from a substantially planar position and to be folded upward into its final shape or position.

The base portion is preferably a substantially planar piece having one or more sides. For example, the base portion could be circular, oval, rectangular, square, triangular, pentagonal, or any other two dimensional shape. Additionally, depending up on the shape, it is preferred that the at least two side panels comprise a number of side panels equivalent to the number of sides of the base portion plane.

It is also preferred to associate a dispersion pad with the frame assembly, and preferably proximate the fluid delivery facilitating means. The dispersion pad may include at least a portion that is porous, wherein the porous portion is associated beneath the fluid-delivery cartridge. To maintain that position, the frame assembly may also include structures and elements for attaching the dispersion pad to the frame assembly. For example, the frame assembly could have an adhesive, heat stake posts, hooks, and clips. Alternatively, the dispersion pad could be folded into and then trapped within the frame assembly by a trapping means, such as slots. Once attached, the dispersion pad preferably at least partially surrounds the frame assembly or is surrounded by the frame assembly.

There are a number of preferred structures for securing the cartridge within the frame assembly. For example, the frame assembly could include a snap and lock apparatus, the apparatus having at least one jaw member for releasably retaining the fluid-delivery cartridge, and preferably a top and a bottom jaw member, which may be associated with a top portion and a bottom portion of the side panels, relatively. The jaw members may be attached to a single side panel, or to different side panels.

In another preferred embodiment, the cartridge may be secured in the frame assembly using an aperture in the base portion of the frame assembly, in combination with one of the jaw members. Alternatively, an aperture could be used with a collar associated with the top of the frame assembly, or with a top portion of the frame assembly that has a concave arcuate shape. The collar is capable of securing the top of the cartridge by itself, while it is preferred that the top portion and the bottom portion include clips if the concave arcuate shape is used. In any case, the aperture, and indeed the collar, preferably includes interference pads to help secure the cartridge within the frame assembly through frictional forces.

If a collar is used, it may have other structural features of note. For example, the collar may include at least one dovetail for associating the frame assembly with an external housing, and preferably includes four dovetails at distally spaced positions around the collar. The collar may be hingedly molded to the at least one side panel, or may be molded to two side panels, if the frame assembly has two side panels, so as to the frame assembly in a final position. In a preferred embodiment, however, the collar is hingedly molded to a single side panel, and includes at least one snap pin hole for engaging one side of the collar to a corresponding snap-fit pin on the frame assembly, to, in turn, place the frame assembly in a final position.

The present device can be used with a number of different types of fluid-delivery cartridges. For example, the fluid-delivery cartridge may be a gravity-fed fluid delivery cartridge, or a fluid-delivery cartridge that delivers fluid against the force of gravity. Alternatively, the fluid-delivery cartridge could include a gas generating cell for facilitating the delivery of fluid from the fluid delivery cartridge. In such an embodiment, it is preferred that the operational resistance of the gas generating cell is controllable to, in turn, regulate the production of gas from the gas generating cell. For example, the device could include a potentiometer associated with the fluid-delivery cartridge that includes a variable resistor and an actuator, wherein the actuator is capable of altering the operational resistance of the gas generating cell.

In another embodiment, it is preferred that the fluid-delivery cartridge additionally includes structures and elements that will help to initiate the operation of the cartridge. For example, the fluid-delivery cartridge could include a breakable barrier associated with a bottom side of the fluid-delivery cartridge, and a piercing member for breaking the breakable barrier to, in turn, initiate the time-release delivery of fluid. The breakable barrier could be, for example, a foil sheet. To break the barrier, it is preferred that the piercing member has at least one piercing point and at least one sloped surface sloping downward and away from the piercing point, and may be integral with the dispersion pad or be a completely separate structure. If the piercing member is a separate structure, it may pierce the breakable barrier by passing through a hole or slit in the dispersion pad, or by passing through both the dispersion pad and the barrier.

In another preferred embodiment, the fluid-delivery cartridge additionally includes structures and elements for delivering a bolus of fluid from the fluid-delivery cartridge. For example, the cartridge could include a button for introducing additional pressure into a fluid reservoir within the fluid-delivery cartridge, or a bolus reservoir proximate an outlet of the fluid delivery cartridge, wherein the bolus reservoir delivers a fluid contained within the bolus reservoir to the outlet upon application of a force to the bolus reservoir. Additionally, the fluid delivery cartridge could have two or more fluid reservoirs, wherein the button or bolus is associated with only one of the reservoirs. Alternatively, one of the reservoirs could hold a bolus of fluid, and could have a separate, breakable barrier so that the entire contents could be released at once.

In another preferred embodiment, the cartridge is only associated with a dispersion pad, that is capable of surrounding at least a portion of the side of the cartridge. The above-described frame assembly can be assembled in several different ways. In one preferred method, the frame is assembled by: (1) providing a foldable frame assembly having means for securing a fluid delivery cartridge, (2) providing a fluid delivery cartridge containing a fluid to be delivered, (3) placing the fluid delivery cartridge within a portion of the foldable frame assembly; (4) securing the fluid delivery cartridge within the foldable frame assembly using the securing means, (5) folding the foldable frame assembly into a final position, and (6) securing the frame assembly in the final position. Alternatively, if the frame assembly is in a fixed, molded shape, the method could comprise the steps of: (1) providing a molded frame assembly in a final position, the frame assembly having means for securing a fluid delivery cartridge, (2) providing a fluid delivery cartridge containing a fluid to be delivered, (3) placing the fluid delivery cartridge within a portion of the frame assembly, and (4) securing the fluid delivery cartridge within the frame assembly.

In either method, it is preferred that, after assembly, a dispersion pad is associated with the frame assembly, either by attaching the pad to the assembly, or by (1) bending the dispersion pad so as to fit within the frame assembly, (2) releasing the dispersion pad once it is situated therein, and (3) trapping the dispersion pad within the frame assembly using a trapping means. The operation of the fluid delivery cartridge can be altered as needed so as to temporarily increase fluid delivery from the cartridge. To do so, in one preferred method, a user can (1) provide a fluid delivery device capable of delivering fluid over time, wherein the device contains a fluid to be delivered to a dispersion pad positioned proximate the fluid delivery device, (2) provide elements and/or structures for delivering a bolus of fluid, (3) can initiate the operation of the fluid delivery device, and then (4) activate the elements and/or structures for delivering a bolus to, in turn, deliver a bolus of fluid. For example, a user can activate the structures by pressing a button to increase the pressure within a fluid reservoir, breaking a breakable barrier of the fluid reservoir, or breaking the seal on a fluid impregnated sponge to, in turn, expose at least a portion of the sponge to ambient air. Alternatively, the cartridge could include a bolus reservoir that releases its contents into the outlet of the cartridge upon application of pressure. Any of these methods can be utilized to increase the immediate fluid flow of the cartridge.

DETAILED DESCRIPTION OF THE INVENTION

While this invention is susceptible of embodiment in many different forms, there is shown in the drawings and will be described in detail, several specific embodiments with the understanding that the present disclosure is to be considered as an exemplification of the principles of the invention and is not intended to limit the invention to the embodiments illustrated.

Figure 1:
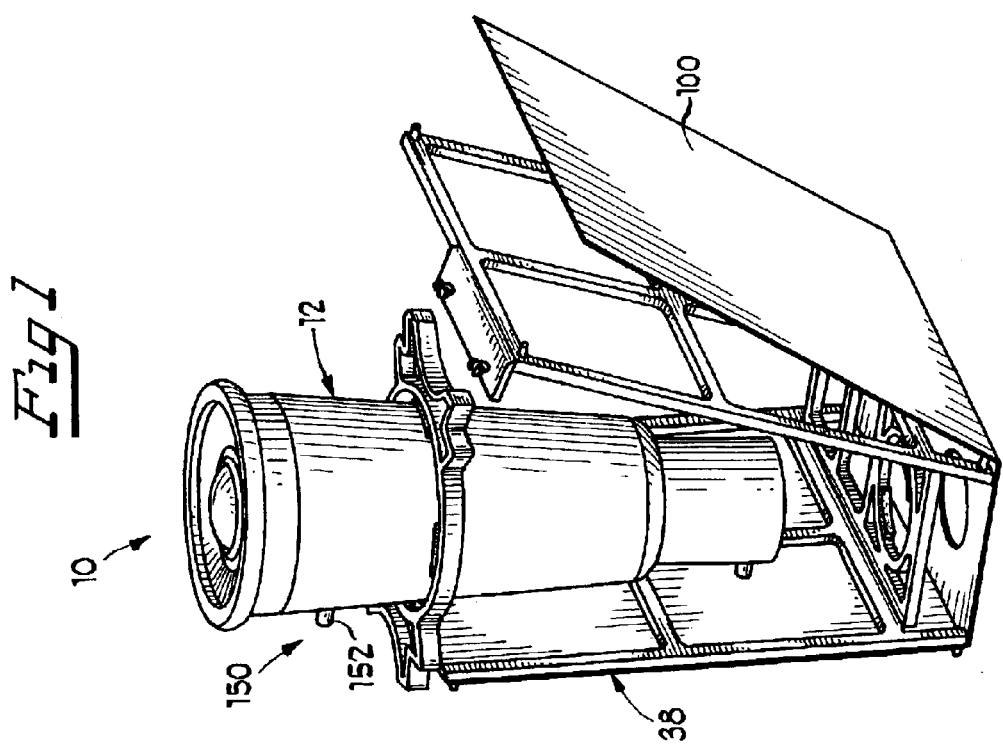
FIG. 1 comprises a perspective view of a fluid delivery system as substantially described herein.

In a preferred embodiment, the present invention comprises a foldable, refillable, sustained-release fluid delivery system for the delivery and then volatilization of a fluid over a period of time. As shown in FIG. 1, fluid delivery system 10 comprises fluid delivery cartridge 12 associated within frame assembly 38 for the time-release delivery of a fluid from within fluid-delivery cartridge 12 onto dispersion pad 100. Once the fluid from fluid-delivery cartridge 12 is delivered onto dispersion pad 100, dispersion pad 100 enables the volatilization of the fluid over a period of time.

Throughout the specification and claims, the present invention will generally be referred to as a fluid delivery system 10 as described above. Generally, however, such systems may additionally be referred to as "refills." The term "refill" may be utilized because the entire system, including the fluid delivery cartridge 12, frame assembly 38, and dispersion pad 100, may be inserted into a product housing for a conventional insecticide/air freshening device.

Fluid-delivery cartridge 12, shown in more detail in FIG. 16, comprises a device for retaining and then delivering a volatile fluid over a period of time. Such cartridges are known in the art, and typically comprise housing 14 containing fluid reservoir 16 for retaining the fluid therein, and restrictor plug 18 that can help to dictate the rate of fluid delivery from fluid reservoir 16. Additionally, housing 14 includes means 22 for delivering the fluid from fluid reservoir 16 out of fluid-delivery cartridge 12. Together, these elements enable the delivery of the fluid, at specified rates, and for a specified period of time.

Housing 14 provides the general shape and structure for fluid-delivery cartridge 12. Typically, as shown in the drawings provided herein, housing 14 is in the shape of a cylinder, with a smaller tapered end within which restrictor plug 18 is situated. The shape of housing 14 is not functionally limited thereto, however, and may be in the form of any number of three-dimensional shapes. Housing 14 holds the desired cartridge shape through the use of rigid or semi-rigid materials, such as, for example, plastics, ceramics, metals and the like, to provide protection for the internal components, and structure and rigidity to fluid-delivery cartridge 12.

Fluid reservoir 16 is situated within and encompasses a majority of the interior space within housing 14 of fluid-delivery cartridge 12. Fluid reservoir 16 provides a secure, non-reactive container for the fluid to be delivered. In order to do so, fluid reservoir 16 may include a lining or housing constructed from inert materials, or at the very least materials that are inert to the fluid contained within fluid reservoir 16. For example, fluid reservoir 16 could be comprised of materials such as plastics, ceramics and the like, or other related materials such as aluminum and stainless steel. If a lining is used for fluid reservoir 16, it can be molded to, plasma deposited, or laminated onto the interior of fluid-delivery cartridge 12.

Fluid reservoir 16 is in fluidic communication with restrictor plug 18. Restrictor plug 18 helps to, along with fluid delivering means 22 (discussed below), control the delivery rate and amount of fluid delivered from fluid reservoir 16. Generally, restrictor plug 18 acts as a barrier to fluid flow out of fluid reservoir 16, except that it includes a tortuous fluid path therethrough. The fluid path generally has a width, depth and length that, depending upon the viscosity of the fluid within fluid reservoir, will allow a predictable amount of fluid to flow from fluid reservoir 16 out of cartridge 12.

A number of other restrictor plug 18 configurations are known in the art, and could similarly be utilized with the presently described fluid-delivery cartridge 12. For example, restrictor plug 18 could also comprise a porous material, such as a sponge, that absorbs and then slowly releases the fluid it contacts. Similarly, restrictor plug 18 could comprise a solid substance having a number of smaller holes (such as a porous plug) through which fluid may be allowed to percolate. In fact, any number of known structures can be utilized that help to control the flow of fluid from fluid reservoir 16 out of fluid delivery device 12.

In a preferred embodiment, fluid-delivery cartridge 12 has breakable seal 20 covering the end of fluid-delivery cartridge 12 to ensure the fluid is maintained within housing 14, and away from outside contaminants until breakable seal 20 is broken. Once breakable seal 20 has been broken, fluid that has already been released through restrictor plug 18 can be immediately released, while fluid in fluid reservoir 16 is simultaneously allowed to flow into restrictor plug 18 and out through breakable seal 20. In order to facilitate this release, breakable seal 20 should be constructed from a thin, inert to the contained fluid (at least), and breakable material, such as plastic film, aluminum foil, or plastic coated aluminum foil.

In another preferred embodiment, fluid delivery cartridge 12 preferably includes means 150 for delivering a bolus of fluid. Because of the extended-release nature of fluid delivery cartridge 12, initiating the delivery of fluid from the cartridge 12 can take anywhere from several hours to several days. In some cases, however, it may be desirable to immediately deliver fluid from fluid delivery cartridge 12. In such a case, bolus delivering means 150 is capable of delivering an immediate and measured amount of fluid out of fluid delivery cartridge 12 as may be needed.

Bolus delivering means 150 is shown in FIG. 1 as comprising button 152. Button 152 may be depressed into fluid delivery cartridge 12 to increase internal pressure within fluid reservoir 16. As pressure is increased within reservoir 16, an equivalent amount of fluid is delivered from fluid delivery cartridge 12. Button 152 may be depressed a single time, or several times, to force fluid from fluid reservoir 16 as needed. Through the use of button 152, delivery of fluid can be initiated well before the operation of fluid delivery cartridge 12 could begin on its own. Of course, other conventional means for forcing a portion of fluid out of a sealed reservoir could be used as well.

Other embodiments could be used to deliver an amount of fluid in a similar manner as button 152. For example, in a preferred embodiment shown in FIG. 16, fluid reservoir 16 could comprise a second, separate reservoir 154 that holds a bolus of fluid for initial delivery. At a desired time, the second reservoir can be tapped so as to deliver the bolus of fluid. The reservoir could be tapped by a button 152', similar to button 152, or could have a separate breakable seal 156 that is capable of releasing the entire contents of the second reservoir. The second reservoir can be associated with restriction plug 18, or may have a direct conduit 158 out of fluid delivery cartridge 12.

Alternatively, the second reservoir could comprise bolus reservoir 154 located proximate an outlet of fluid delivery cartridge 12, either inside cartridge 12 or outside that structure, wherein bolus reservoir 154 comprises a small amount of fluid that releases into the outlet upon application of a pressure.

As another alternative embodiment, fluid delivery cartridge 12 may be associated with a sealed, fluid-impregnated sponge 160. The sponge may be associated with the external area of housing 14, or may be incorporated all or partly into the housing 14. Either way, the sponge should be exposed to the ambient air surrounding cartridge 12. Bolus delivering means 150, in this embodiment, comprises a means for breaking the seal surrounding the sponge so as to expose the fluid-impregnated sponge immediately to the surroundings. For example, the seal could be broken by a pull strip 162, zipper, puncturing device, or other conventionally known structures.

The above embodiments describe a structural system that enables fluid delivery cartridge 12 to begin emitting fluid on a much shorter time scale than the cartridge 12 could alone. Although the above-described structures present some possible embodiments for the delivery of the bolus, bolus delivering means 150 could comprise any number of other conventionally known structures/methods, as would be known by one of ordinary skill in the art.

Until now, only the basic component elements of fluid-delivery cartridge 12 have been discussed. In order to assist and to help control the delivery of fluid, however, a preferred embodiment of the invention includes means 22 for delivering fluid out of fluid-delivery cartridge 12. Such fluid-delivering means can comprise, for example, a gravity-feed device, a device for delivering fluid against the force of gravity, such as is shown in U.S. Pat. No. 6,045,055, an air pump, and a gas generating cell. Fluid delivery means 22 provides the necessary or additional forces needed to deliver a proper amount of fluid over a period of time.

One particularly interesting embodiment of the fluid-delivery cartridge 12 with fluid delivery means 22 is when fluid delivery means 22 comprises gas generating cell 30, as is shown in FIG. 10. Generally, gas generating cell 30 has a positive terminal 32 on its top portion, and a negative terminal 34 that is electrically connected through housing 14. Gas generating cell 30, when placed within a completed electrical circuit, produces a gas as a product of an electrochemical reaction. Examples of acceptable gas generating cells include, but are not limited to, those found in U.S. Pat. Nos. 5,593,552 and 5,707,499.

Depending upon the type of gas generating cell 30 selected for use with fluid-delivery cartridge 12, a shield 36 may be necessary for the prolonged life of gas generating cell 30. Shield 36, shown in FIG. 16, is placed between gas generating cell 30 and fluid reservoir 16, to prevent the influx of fluid into gas generating cell 30, while simultaneously allowing gas generated within cell 30 out into housing 14. Further, shield 36 can act as a gasket, ensuring the seal between gas generating cell 30 and fluid reservoir 16 is secure. A number of materials can be utilized for shield 36, including polypropylene and polyethylene. It is important that the shield should be gas permeable and substantially impermeable to moisture. Examples of acceptable shields are identified in U.S. Pat. No. 5,707,499.

Together, the above elements form a basic fluid delivery cartridge 12 for the time release delivery of a fluid contained therein. Such devices can be utilized for a wide variety of applications, from the delivery of insecticide, to air freshening liquids, as well as other volatile liquids. It is preferable to incorporate fluid delivery cartridge 12 into a product housing (not shown), which provides a reusable structure for fluid delivery, into which new replacement fluid delivery cartridges 12 may be placed when the old ones are exhausted. In order to facilitate the use of the cartridges within product housings, fluid delivery cartridge 12 is secured within frame assembly 38, shown in FIGS. 2–5. Frame assembly 38 provides a secured, easy to handle, rigid or semi-rigid structure for support of fluid-delivery cartridge 12, and subsequent insertion into a product housing.

Frame assembly 38 is shown in one preferred embodiment in FIG. 2. In that embodiment, frame assembly 38 comprises base portion 40, side panels 48, and means 70 for securing the fluid-delivery cartridge within fame assembly 38. These elements together form the final product shape of frame assembly 38. The entire assembly provides a secure retaining area for fluid delivery cartridge 12, while giving structure to the entire device through the use of rigid or semi-rigid materials.

Base portion 40 is shown in FIG. 2 as a substantially rectangular, planar piece of material having an outer frame 41, and cross beams 42 to provide structural support. Alternatively, and not shown, base portion 40 could comprise a single, solid planar piece of material. Base portion 40 additionally comprises means 43 for facilitating the delivery of fluid released from fluid-delivery cartridge 12 out and away from frame assembly 38, which is shown as aperture 44 in FIG. 2. As an alternative, and as shown in FIG. 7, means 43 for facilitating the delivery of fluid released from fluid delivery cartridge 12 could comprise pre-scored, puncture-ready shapes, such as a star-like shape shown in FIG. 7, which may be subsequently pierced and split by piercing member 140 (discussed below). In any case, fluid delivery cartridge 12 is generally associated with base portion 40 proximate delivery facilitating means 43 to enable any fluid released from cartridge 12 to be subsequently released from frame assembly 38.

Outer frame 41 of base portion 40 is shown in one preferred configuration in FIG. 2 as a substantially planar rectangular structure. It should be noted that a planar structure is shown simply as one preferred embodiment, but that slight curvatures and curved structures could similarly suffice. Additionally, it is also contemplated that base portion 40, and indeed outer frame 41 of base portion 40, could comprise a number of different shapes and sizes depending upon the intended environment for the entire fluid delivery system 10. For example, and as shown in FIG. 8, base portion 40 could comprise a triangle, pentagon, hexagon, heptagon, octagon, or any number of other polygonal shapes. Similarly, base portion 40 could be in the shape of a circle, oval, or other rounded shape. In fact, almost any shape is acceptable as long as the base portion 40 provides a sufficient cross-sectional footprint that the bottom area of fluid delivery cartridge 12 is supported.

Depending upon the particular shape of base portion 40, a number of side panels 48 are associated therewith.

Particularly, at least one side panel 48 is associated with the base portion 40 to form an enclosure within which the cartridge 12 may be secured. In a preferred embodiment, at least two side panels 48 are associated with base portion 40, and more preferably a number of side panels equivalent to the number of sides of base portion 40, less at least one, are associate with base portion 40. By providing a number of side panels 48 to base portion, while at least leaving side of base portion 40 clear, cartridge 12 can be inserted, removed, and replaced within frame assembly 38 over time.

One preferred embodiment is shown in FIG. 2, in which base portion 40 is a rectangle, and side panels 48 are located on opposite sides of base portion 40. The side panels 48 are constructed from the same or similar materials as base portion 40, having an outer frame 49 with cross beams 50 across the middle section for support. Side panels 48 may be associated with base portion 40 in a number of ways. For example, in one embodiment, side panels 48 are integrally molded with base portion 40 in the final position, as seen in FIG. 2. Alternatively, side panels 48 are hingably associated by hinge 54 to base portion 40 so that the entire frame assembly 38 can be folded from a substantially flat position into the final assembled position (See, e.g., FIG. 6).

Preferably, side panels 48 additionally include leg extensions 56, which may be used to properly position dispersion pad 100 (discussed below) around frame assembly 38, and to provide a stand for frame assembly 38. To further assist the association of dispersion pad 100 with frame assembly 38, frame assembly 38 additionally comprises means 64 for attaching dispersion pad 100 to frame assembly 38. Attaching means 64 is shown in FIGS. 2–5 as comprising heat stake posts 66. Heat stake posts 66 facilitate the attachment of dispersion pad 100 to frame assembly 38 by providing a conical shape that can protrude through dispersion pad 100, and then be heat-sealed thereafter, securing the dispersion pad 100 on frame assembly 38. Alternatively, attaching means 64 could comprise an adhesive for securing to the frame assembly 38.

Once frame assembly 38 is properly assembled, either in an integrally molded embodiment, or in a folded-frame assembly, fluid delivery cartridge 12 can be inserted and secured into frame assembly 38 using securing means 70. Securing means 70 has a number of preferred embodiments, shown in FIGS. 2–5. In one preferred embodiment, shown in FIG. 2, frame assembly 38 comprises aperture 78 in base portion 40, and collar 88 attached to upper section 62 of frame assembly 38. Together, aperture 78 and collar 88 allow a replaceable cartridge to be inserted into and secured within frame assembly 38.

Aperture 78 comprises an opening within base portion 40 into which the bottom section of cartridge 12 is inserted. Generally, aperture 78 should approximately correspond to the shape and size of the bottom of fluid delivery cartridge 12, although slightly larger in diameter. To help secure cartridge 12 within aperture 78, aperture 78 additionally includes at least one interference pad 80 along its circumference. Interference pad 80 may comprise a rubberized piece of material that provides a frictional retaining force after insertion of cartridge 12. Preferably, aperture 78 includes four separate interference pads 80, spaced equally around the aperture's circumference.

Collar 88 also conforms substantially to the cross sectional shape of cartridge 12, but to the top of cartridge 12 instead of the bottom. If a foldable configuration for frame assembly 38 is utilized (i.e. if side panels 48 and base portion 40 are connected using hinges 54), collar 88 can either be integrally molded onto the top of one of side panels 48, or can be hingedly attached thereto via hinge 90. Alternatively, if frame assembly 38 is already molded into the final position, collar 88 is preferably associated with one of side panels 48 via hinge 90 to accommodate the insertion of cartridge 12 into frame assembly 38.

In both these embodiments, the opposing side of collar 88 away from the molded/hinged side includes at least one snap pin hole 94, which is shown in more detail in FIG. 9. Snap pin hole 94 comprises an aperture in collar 88 that approximately corresponds in size and location to a snap-fit pin 96 located on the top of one side panel 48. Snap-fit pin 96 includes two flexible halves with a space therebetween, wherein the flexible halves are capable of bending towards one another while being inserted into snap pin hole 94, and then flexing back to secure collar 88 against the top of side panel 48. Through the use of the snap pin hole 94/snap-fit pin 96 combination, the final completed frame assembly can be opened and closed so as to allow the insertion of a cartridge 12 therein, while still ensuring the secure retainment of that cartridge 12 within frame assembly 38.

In an alternative and preferred embodiment, collar 88 is not attached to side panels 48 at all, but instead includes sufficient snap pin holes 94 to be secured to two or more side panels 48, or sufficient side panels 48 to assure maintenance of the rigidity of the structure and the securement of the cartridge 12 therein.

Collar 88 preferably also includes at least one dovetail 92 thereon. Dovetails 92 comprise shaped extensions protruding outward radially from collar 88, and are generally formed from the same or similar materials as collar 88. Dovetails 92 are generally utilized to help mount cartridge 12, and frame assembly 38, within a product housing.

A second embodiment of the cartridge securing means 70 is shown in FIG. 3 as comprising a snap and lock apparatus having at least two jaw members 72 that are capable of releasably securing cartridge 12 within frame assembly 38. Jaw members 72 comprise a resilient, semi-rigid material, such as plastic and the like, which is formed into a semi-circular shape approximating the diameter/shape of cartridge 12. Tips 73 of jaw member 72 flex outward upon contact with cartridge 12, allowing cartridge 12 to pass into interior 74 of jaw member 72. Thereafter, tips 73 flex back into the original position, securing cartridge 12 therein.

Preferably, at least two jaw members 72 are molded into or associated with one or more of side panels 48. In one preferred embodiment, jaw members 72 comprise a top 75 and a bottom 76 jaw member attached to top 51 and bottom 52 portions of a single side panel 48 respectively. Alternatively, depending upon the specific shape of base portion 40, and thus the overall shape of frame assembly 38, jaw members 72 may be placed on different side panels 48. For example, opposing side panels 48 of a rectangularly-shaped, folding frame assembly 38 could include jaw members 72 so that, after inserting cartridge 12 into at least one of the jaw members attached to a single side panel 48, the opposing side panel 48 could be folded up and into cartridge 12, locking cartridge 12 into place with the second jaw member 72.

A third embodiment of the cartridge securing means 70 is shown in FIG. 4 as a combination of the snap and locking jaw members 72, and an aperture 78 within base portion 40. In this embodiment, after fluid-delivery cartridge 12 is inserted into aperture 78, securing the bottom of cartridge 12 therein, the top portion of cartridge 12 may be secured also using jaw member 72. Depending upon the nature of frame assembly 38 (folding or non-folding), cartridge 12 may be secured by jaw member 72 upon insertion into aperture 78, or may be secured after insertion into aperture 78 by folding frame assembly 38 together. As with the embodiment shown in FIG. 2, it is preferred that aperture 78 additionally includes interference pads 80 for frictionally securing cartridge 12 therein.

A fourth embodiment of cartridge securing means 70 is shown in FIG. 5. In that embodiment, frame assembly 38 additionally includes top portion 58, which at least partially covers and spans across the top of frame assembly 38, and is associated with side panels 48 using any one of the above-discussed means (molding, hinging, snap pin hole/snap fit pin, etc.). Top portion 58 preferably has a convex, arcuate shape, wherein the middle of the arcuate shape approximately coincides with fluid delivery facilitating means 43 of base portion 40. Facilitating means 43 preferably comprises aperture 78, but may additionally comprise scored slits 46, as discussed above. Cartridge 12 is placed at the middle of the arcuate shape, and over facilitating means, and is secured there using clip members 82.

A top clip member 84 is secured to the arcuate shape of top portion, and secures the top of cartridge 12 thereto. A bottom clip member 86 is secured to base portion 40, and further secures bottom of cartridge 12 in an appropriate position. Both top clip member 84 and bottom clip member 86 may be attached to frame assembly 38 using any number of conventional means.

Using any of the above embodiments, fluid-delivery cartridge 12 can be secured to and within frame assembly 38. Once in place, fluid-delivery cartridge 12 can deliver its contained fluid, at a predetermined rate, out of frame assembly 38 and onto dispersion pad 100.

Dispersion pad 100 (as shown in FIG. 13–15) comprises a sheet of material that is capable of receiving the fluid delivered from fluid-delivery cartridge 12, and retaining the fluid therein for a period of time sufficient to allow the fluid to evaporate. The sheet can be of varying lengths, widths, and thicknesses, and can be formed from a number of known materials, including woven or non-woven natural or synthetic fibers, sintered porous polypropylene, or paper.

Preferably, dispersion pad 100 has at least a portion which is porous (called porous portion 101) which is especially configured for receiving and retaining fluid delivered from cartridge 12. Porous portion 101 may comprise the entire length, width, and thickness of the sheet of dispersion pad 100, or instead may be a portion of pad 100 located only underneath the fluid delivery facilitating means 43.

Dispersion pad 100 is preferably large enough that at least a portion of dispersion pad 100 extends beyond the area immediately underneath base portion 40, to extend at least partially up and around side portions 48 of frame assembly 38. Preferably, the dispersion pad 100 extends along the entire outer portion of side panels, and may be secured thereon using one of any number of conventional means, for example, heat stake posts 66, hooks, clips or adhesive. Alternatively, as shown in FIG. 17, dispersion pad 100 could comprise a resilient, material having some amount of spring, wherein dispersion pad 100 may be flexed and inserted into frame assembly 38, where it will flex back into position so as to be trapped in place by trapping means 160. Trapping means 160 could comprise any number of means for securing the folded dispersion pad 100 within frame assembly 38, such as slots 162 shown in FIG. 17. To do so, dispersion pad 100 may include fold lines corresponding to the intersection joints between side panels 48, and base portion 40, or may be folded into frame assembly 38 so as to be shaped at least partially thereby.

In order to aid the folding of dispersion pad 100, it may be necessary to include a guide for folding dispersion pad 100 into an appropriate shape, such as a mandrel. Other conventional structures could similarly be used as well.

Due to the porous nature of dispersion pad, and upon delivery of fluid to dispersion pad 100, a wicking effect allows fluid to flow from the initial spot of delivery away and to the distally located areas substantially surrounding side panels 48. As the fluid flows, more and more volatile fluid is exposed to the surrounding air, increasing the total amount of fluid that is evaporated.

In one preferred embodiment, shown in FIG. 13, dispersion pad 100 may or may not be associated with frame assembly 38. Instead, dispersion pad 100 is associated solely with fluid delivery cartridge 12. In this embodiment, dispersion pad 100 is manufactured at least partially from a material having rigidity or a semi-rigidity, and has a length/width such that it extends at least partially around the side portions of fluid delivery cartridge 12. The rigidity/semi-rigidity of the dispersion pad 100 allows the pad 100 to remain upright and adjacent the sides of cartridge 12. Alternatively, dispersion pad 100 can be formed from a sheet of material that is capable of being folded into a shaped structure that at least partially encompasses the cartridge 12. In one such embodiment, shown in FIG. 15, dispersion pad 100 is associated with a base section 104 located underneath fluid-delivery cartridge 12, a backing section 105 running behind and parallel to the cartridge 12, and two side sections 106 folded rectangularly around cartridge 12. In such an embodiment, dispersion pad 100 preferably includes vertical fold lines 103 running along its length and parallel to the length of cartridge 12, enabling the sides 106 to fold in at right angles to the backing section 105. Further, dispersion pad 100 includes horizontal fold lines 102 at the junction between the vertical portions of dispersion pad 100 and base section 104. In any case the shape of dispersion pad 100 allows the pad to increase the volatilization of fluid through the wicking effects, without the need for a rigid frame structure such as frame assembly 38.

In another preferred embodiment (FIG. 14), dispersion pad 100 is folded so that its distal ends 107 meet the top portion of cartridge 12. In this embodiment, additional strength is provided to dispersion pad 100 through its association with both the bottom and the top of fluid-delivery cartridge 12.

In one preferred embodiment of the invention, shown in FIG. 10, fluid-delivery cartridge 12 includes gas generating cell 30, and frame assembly 38 additionally comprises potentiometer 110. Potentiometer 110 is electrically attached to positive 32 and negative 34 terminals of gas generating cell 30. As gas generating cell 30 operates electrochemically, the amount of current that flows through cell 30 dictates the amount of gas released therefrom, and, in turn, the rate of delivery of fluid from cartridge 12. Potentiometer 110 provides a means for controlling the rate of gas generating cell 30 operations and, therefore, the delivery rate of fluid from cartridge 12.

Potentiometer 110 enables the rate of delivery of fluid to be adjusted during the operation of the fluid-delivery cartridge 12. It should be noted, however, that adjustment of the operational rate of cartridge 12 due to changes in atmospheric conditions is not necessarily required to maintain a consistent flow of fluid. As changes in temperature and pressure occur in the environment surrounding cartridge 12, the rate of delivery of fluid from cartridge 12 can be affected. However, brief increases and decreases in delivery rates will average out over time.

Potentiometer 110 is shown in FIG. 10 as comprising potentiometer mounting surface 132 onto which substrate 112 is mounted containing the wiring of potentiometer 110. Substrate 112 includes variable resistor 114, metallic traces 116 leading from resistor 114, and contacts 118 for connecting to gas generating cell 30 and terminals 32, 34. The potentiometer 110 regulates the operating current of the system by changing the resistance applied across the anode and cathode of the gas generating cell.

To facilitate the resistance change, potentiometer 110 additionally includes switch apparatus 122. Switch apparatus 122 includes slider cover plate 124, which lies over substrate 112, and helps to hold substrate 112 in place using guide bars 126. Cover plate 124 includes selection slider 128 within slide channel 130, which comes into contact with variable resistor 114, controlling the effective resistance of that element.

The entire potentiometer 110 is mounted to frame assembly 38 using mounting surface 132. Substrate 112 is mounted to mounting surface 132 using, for example, heat stakes that pass through mounting holes 120 in substrate 112 surface. Contacts 118 pass through contact opening 134 to be mounted on contact mounting surface 136, located above cartridge 12, using mounting stakes 138. Thereafter, contacts 118 can be placed into electrical contact with positive 32 and negative 34 terminals of gas generating cell, for controlling the operating current of that device. Although a specific potentiometer has been disclosed, conventional current limiting devices are also contemplated for use.

In operation, to initiate the operation of fluid delivery cartridge 12, piercing member 140 is introduced to (if necessary) pierce through fluid delivery facilitating means 43, and into and through breakable seal 20 on cartridge 12, initiating delivery of fluid therefrom. Initiation, of course, may include other procedures, such as, for example, the initiation of current flow through gas generating cell 30. In any case, operation of fluid delivery system 10 begins, in part, with the piercing of breakable seal using piercing member 140.

Piercing member 140 is shown in FIG. 11 as a single, self-contained piece having base 142 with piercing design 143 thereon. Piercing design 143, generally, comprises at least one piercing point 144, and at least one sloped surface 146 sloping downward and away from the piercing point 144. Piercing point 144 enables piercing member 140 to pass upward and through breakable seal 20. After insertion into the cartridge 12, sloped surfaces 146 provide a flow path for fluid out of cartridge and away from piercing point 142, to ensure the fluid comes into contact with dispersion pad 100.

Piercing design 143 has a number of different possible configurations, some of which are shown in FIGS. 12(a)–12(e). Each design includes a piercing point 144, and a sloped surface 146, as described above. Each of these designs was tested for its efficacy in not only piercing breakable barrier 20, but in ensuring that the maximum amount of fluid was allowed to flow therefrom. In an alternative embodiment, piercing member 143 could pierce both barrier 20, and dispersion pad 100. It was found that the embodiment shown in FIG. 12(d) provided the maximum fluid flow from cartridge 12.

Piercing member 143 may be used as a completely separate piece to pierce breakable seal 20. To facilitate the piercing, dispersion pad 100 preferably includes hole 108 that approximates the size of the cross section of piercing design 143. Piercing member 143 may be inserted into and through hole 108, but is maintained there afterwards to ensure proper distribution of fluid out of cartridge 12 and onto dispersion pad 100.

Alternatively, and as shown in FIG. 13, piercing member 143 can be integrated into dispersion pad 100. Such a design may be especially useful if dispersion pad 100 comprises the relatively rigid embodiment described above. Even if dispersion pad 100 is not rigid, however, integration of piercing member 143 into the structure of pad 100 enables the entire design to be associated with frame assembly 38, and to initiate operation of the fluid delivery system 10 at the same time.

The above-described structure can be manufactured and assembled in a number of different ways. One preferred manner of manufacture comprises the steps of: (1) providing a foldable frame assembly having a base portion 40, at least one side panel 48, and means 70 for securing a fluid delivery cartridge 12, (2) providing a fluid delivery cartridge 12 containing a fluid to be delivered, (3) placing the fluid delivery cartridge 12 within a portion of the foldable frame assembly 38, (4) securing the fluid delivery cartridge 12 within the foldable frame assembly 38, (5) folding the foldable frame assembly 38 into a final position, and (6) securing the frame assembly 38 in the final position. The same steps can be undertaken using a molded, pre-set frame assembly 38, in which the step of folding then becomes unnecessary.

The foregoing description merely explains and illustrates the invention and the invention is not limited thereto except insofar as the appended claims are so limited, as those skilled in the art that have the disclosure before them will be able to make modifications without departing from the scope of the invention.

What is claimed is:

1. A framed fluid delivery device, comprising:
    a fluid-delivery cartridge for the delivery of a fluid contained therein over a period of time; and
    a frame assembly for retaining the fluid delivery cartridge, comprising means for securing the fluid-delivery cartridge within the frame assembly, wherein the securing means comprises a snap and lock apparatus associated with the frame assembly, the snap and lock apparatus comprising at least one jaw member for releasably retaining the fluid-delivery cartridge; the frame assembly further comprising:
    a base portion having a means for facilitating the delivery of fluid released from the fluid-delivery cartridge; and
    at least one side panel associated with the base such that the securing means secures the fluid-delivery cartridge proximate the released fluid delivering means; and
    wherein the at least one jaw member comprises a top and a bottom jaw member, wherein the top jaw member is associated with a top portion of the at least one side panel, and the bottom jaw member is associated with a bottom portion of the at least one side panel.

2. The device according to claim 1, at least one side panel comprises at least two side panels, wherein the top and bottom jaw members are associated with the same side panel.

3. The device according to claim 1, wherein the at least one side panel comprises at least two side panels, wherein the top and bottom jaw members are associated with different side panels.

4. A framed fluid delivery device, comprising:
   a fluid-delivery cartridge for the delivery of a fluid contained therein over a period of time;
   a frame assembly for retaining the fluid delivery cartridge, comprising means for securing the fluid-delivery cartridge within the frame assembly; and
   a dispersion pad associated with the frame assembly;
   wherein the dispersion pad is trapped within the frame assembly by means for trapping the dispersion pad, the trapping means comprising slots associated with the frame assembly, the frame assembly comprising:
      a base portion having a means for facilitating the delivery of fluid released from the fluid-delivery cartridge; and
      at least one side panel associated with the base such that the securing means secures the fluid-delivery cartridge proximate the released fluid delivering means
         wherein the securing means additionally comprises an aperture in the base portion of the frame assembly, wherein the aperture is fanned to substantially correspond to a cross-sectional shape of a bottom side of the fluid-delivery cartridge.

5. The device according to claim 4, wherein the securing means secures the fluid-delivery cartridge proximate the released fluid delivering means.

6. The device according to claim 5, wherein the base and the at least one side panel are hingably associated with each other so that they may be folded or bent into a final position from an initially substantially planar position.

7. The device according to claim 5, wherein the base portion comprises a substantially planar piece having one or more sides.

8. The device according to claim 5, wherein the at least one side panel comprises at least two side panels.

9. The device according to claim 8, the at least two side panels comprise a number of side panels equivalent to the number of sides of the base portion plane.

10. The device according to claim 5, wherein the frame assembly additionally comprises leg extensions associated with at least one of the base portion and the at least one side panel.

11. The device according to claim 4, wherein the securing means secures the fluid-delivery cartridge proximate the released fluid delivering means, and the dispersion pad is associated proximate the fluid delivery facilitating means.

12. The device according to claim 11, wherein the dispersion pad includes at least a portion that is porous, wherein the porous portion is associated beneath the fluid-delivery cartridge.

13. The device according to claim 4, wherein the frame assembly includes means for attaching the dispersion pad to the frame assembly.

14. The device according to claim 13, wherein the dispersion pad attaching means comprises an adhesive.

15. The device according to claim 13, wherein the dispersion pad attaching means is selected from at least one of the group consisting of heat stake posts, hooks, and clips.

16. The device according to claim 4, wherein the dispersion pad at least partially surrounds the frame assembly, or is at least partially surrounded by the frame assembly.

17. The device according to claim 4, wherein the aperture includes at least one interference pad for frictionally securing the fluid-delivery cartridge therein upon insertion.

18. The device according to claim 4, wherein the fluid-delivery cartridge is a gravity-fed fluid delivery cartridge.

19. The device according to claim 4, wherein the fluid-delivery cartridge comprises a gas generating cell for facilitating the delivery of fluid from the fluid delivery cartridge.

20. The device according to claim 19, additionally comprising means for regulating the operational resistance of the gas generating cell to, in turn, regulate the production of gas from the gas generating cell.

21. The device according to claim 20, wherein the resistance regulating means comprises a potentiometer associated with the fluid-delivery cartridge.

22. The device according to claim 21, wherein the potentiometer includes a variable resistor and an actuator wherein the actuator is capable of altering the operational resistance of the gas generating cell.

23. The device claim 4, wherein the fluid-delivery cartridge additionally comprises means for initiating the time-release delivery of fluid, wherein the initiating means comprises:
   a breakable barrier associated with a bottom side of the fluid-delivery cartridge; and
   a piercing member for breaking the breakable barrier to, in turn, initiate the time-release delivery of fluid.

24. The device according to claim 23, wherein the breakable barrier comprises a foil sheet.

25. The device according to claim 23, wherein the piercing member has at least one piercing point and at least one sloped surface sloping downward and away from the piercing point.

26. The device according to claim 23, wherein the dispersion pad is located proximate the fluid delivery facilitating means, wherein the piercing member is integral with the dispersion pad.

27. The device according to claim 23, wherein the dispersion pad is located proximate the fluid delivery facilitating means, wherein the piercing member comprises a separate structure than the dispersion pad, and the dispersion pad additionally comprises a hole for placing the piercing member into contact with the breakable barrier.

28. The device according to claim 23, wherein the dispersion pad is located proximate the fluid delivery facilitating means, wherein the piercing member comprises a separate structure than the dispersion pad that is capable of piercing both the dispersion pad and the breakable barrier.

29. The device according to claim 4, wherein the fluid-delivery cartridge comprises means for delivering a bolus of fluid from the fluid-delivery cartridge.

30. The device according to claim 29, wherein the bolus delivering means comprises a button for introducing additional pressure into a fluid reservoir within the fluid-delivery cartridge.

31. The device according to claim 29, the bolus delivering means comprises a bolus reservoir proximate an outlet of the fluid delivery cartridge, wherein the bolus reservoir delivers a fluid contained within the bolus reservoir to the outlet upon application of a force to the bolus reservoir.

32. The device according to claim 29, wherein the fluid cartridge comprises at least two fluid reservoirs, wherein the delivering means is associated with at least one of the two fluid reservoirs.

33. The device according to claim 32, wherein the delivering means comprises a button for introducing additional pressure into the fluid reservoir.

34. The device according to claim 32, wherein the delivering means comprises a breakable seal associated with the fluid reservoir.

35. A framed fluid delivery device, comprising:
a fluid-delivery cartridge for the delivery of a fluid contained therein over a period of time; and
a frame assembly for retaining the fluid delivery cartridge, the frame assembly comprising:
- a base portion having a means for facilitating the delivery of fluid released from the fluid-delivery cartridge;
- at least one side panel associated with the base;
- a top portion, wherein the top portion has a concave arcuate shape; and
- means for securing the fluid-delivery cartridge within the frame assembly, wherein the securing means comprises at least two clip members for securing a bottom side of the fluid-delivery cartridge to the base portion, and for scouring a top side of the fluid-delivery cartridge to the top portion of the flame assembly, the securing means securing the fluid-delivery cartridge proximate the released fluid delivering means.

36. A framed fluid delivery device, comprising:
a fluid-delivery cartridge for the delivery of a fluid contained therein over a period of time; and
a frame assembly for retaining the fluid delivery cartridge, the frame assembly comprising:
- a base portion having a means for facilitating the delivery of fluid released from the fluid-delivery cartridge;
- at least one side panel associated with the base; and
- means for securing the fluid-delivery cartridge within the frame assembly, wherein the securing means comprises an aperture in the base portion of the frame assembly, and a collar associated with an upper section of the frame assembly, wherein the aperture and the collar are configured so as to substantially correspond to a shape of the fluid-delivery cartridge.

37. The device according to claim 36, wherein at least one of the aperture and the collar comprise at least one interference pad for frictionally securing the fluid-delivery cartridge within the aperture and/or collar.

38. The device according to claim 36, wherein the collar additionally includes at least one dovetail for associating the frame assembly with an external housing.

39. The device according to claim 38, wherein the collar includes four dovetails at distally spaced positions around the collar.

40. The device according to claim 36, wherein the collar is hingedly molded to the at least one side panel.

41. The device according to claim 36, wherein at least one side panel includes at least two side panels, and the collar is molded to both of the at least two side panels, placing the frame assembly in a final position.

42. The device according to claim 36, wherein at least one side panel includes at least two side panels, and the collar is hingably molded to one of the at least two side panels, and wherein the collar further includes at least one snap pin hole for engaging an unmolded side of the collar to a corresponding snap-fit pin on the frame assembly, to, in turn, place the frame assembly in a final position.

43. A refill for a liquid air freshener or insecticidal device comprising a cartridge containing a volatile liquid composition to be evaporated and a porous pad positioned, in use, to receive the liquid composition as it is slowly released from the cartridge; wherein the porous pad is a part of a sheet of material which is folded along at least one fold line which, in use, extends substantially vertically to at least partially surround the cartridge, the sheet of material and cartridge being supported in a frame, wherein the sheet of material comprises the porous pad, a rear panel and two side panels which are folded inwardly along the vertical fold lines towards one another from opposite sides of the rear panel.

44. A refill according to claim 43, wherein the porous pad is folded attached to a bottom edge of the rear panel along a fold line which, in use, is substantially horizontal.

45. A refill according to claim 43, wherein the porous pad is attached to one or both bottom edges of the side panels along a fold line which, in use, is substantially horizontal.

* * * * *